US008142368B2

(12) United States Patent
Egorov et al.

(10) Patent No.: US 8,142,368 B2
(45) Date of Patent: Mar. 27, 2012

(54) METHOD OF CHARACTERIZATION AND DIFFERENTIATION OF TISSUE

(75) Inventors: Vladimir Egorov, Princeton, NJ (US); Armen P. Sarvazyan, Lambertville, NJ (US)

(73) Assignee: Artann Laboratories Inc., Trenton, NJ (US)

( * ) Notice: Subject to any disclaimer, the term of this patent is extended or adjusted under 35 U.S.C. 154(b) by 59 days.

(21) Appl. No.: 12/244,235

(22) Filed: Oct. 2, 2008

(65) Prior Publication Data

US 2010/0087756 A1    Apr. 8, 2010

(51) Int. Cl.
| A61B 5/00 | (2006.01) |
| A61B 5/103 | (2006.01) |
| A61B 17/00 | (2006.01) |
| G01N 33/48 | (2006.01) |
| G01B 3/00 | (2006.01) |
| G01B 5/28 | (2006.01) |
| G01B 5/30 | (2006.01) |
| G01L 1/00 | (2006.01) |
| G01L 3/00 | (2006.01) |
| G01L 5/00 | (2006.01) |

(52) U.S. Cl. .......... 600/587; 600/306; 606/201; 702/21; 702/33; 702/36; 702/42

(58) Field of Classification Search .................. 600/306, 600/587; 606/201; 702/21, 33, 36, 42
See application file for complete search history.

(56) References Cited

U.S. PATENT DOCUMENTS

| 5,840,023 | A | * | 11/1998 | Oraevsky et al. ............. 600/407 |
| 5,860,934 | A | | 1/1999 | Sarvazyan |
| 6,063,031 | A | | 5/2000 | Cundari |
| 6,091,981 | A | * | 7/2000 | Cundari et al. ............... 600/407 |
| 6,488,626 | B1 | * | 12/2002 | Lizzi et al. .................... 600/437 |
| 6,595,933 | B2 | | 7/2003 | Sarvazyan |
| 6,620,115 | B2 | | 9/2003 | Sarvazyan |
| 6,832,111 | B2 | | 12/2004 | Tu |
| 6,868,342 | B2 | | 3/2005 | Mutter |
| 7,292,737 | B2 | | 11/2007 | Zhou |
| 7,492,931 | B2 | * | 2/2009 | Sabol et al. ................... 382/128 |
| 2007/0123773 | A1 | * | 5/2007 | Fuchs et al. .................. 600/410 |
| 2009/0083075 | A1 | * | 3/2009 | Henschke et al. ............... 705/3 |

* cited by examiner

*Primary Examiner* — Max Hindenburg
*Assistant Examiner* — Sean Dougherty
(74) *Attorney, Agent, or Firm* — Boris Leschinsky

(57) ABSTRACT

A novel method for soft tissue characterization includes obtaining a sequence of surface stress patterns as a function of an increasing compression force when a probe is pressed against the tissue over the location of the lesion of interest. A number of elasticity features are then calculated to characterize the tissue and the lesion located therein including strain hardening, loading curve average slope, lesion peak signal under a predetermined load, tissue heterogeneity, lesion shape and lesion mobility. At least three elasticity features are provided as an input to a statistical Bayesian classifier trained on a clinical database to calculate the probability of the lesion being benign or malignant. Additional patient-related parameters may be further provided as inputs to the classifier to increase the accuracy of differentiation between benign and malignant lesions. These parameters include a family history of cancer disease, a patient-inherited genetic factor, a history of said tissue related diseases, patient's age, patient's weight, and patient's lifestyle and dietary factors. The method of the invention along with other non-invasive examinations of lesions may help in reducing the rate of biopsies, specifically breast tissue biopsies.

24 Claims, 4 Drawing Sheets

METHOD OF CHARACTERIZATION AND DIFFERENTIATION OF TISSUE

FIELD OF THE INVENTION

The present invention relates to medical imaging and tissue characterization methods. More particularly, the invention establishes a method of characterization and differentiation of soft tissue pathologies.

BACKGROUND OF THE INVENTION

Manual palpation of human tissues and organs has been used for a long time as a preliminary diagnostic tool. It is known that development of certain pathologies causes tissue to harden, that is, the elasticity modulus, E, is a highly variable and disease-sensitive physical parameter of soft tissues [Sarvazyan A. P. Elastic properties of soft tissue.—In: Handbook of Elastic Properties of Solids, Liquids and Gases, Volume III, Chapter 5, eds. Levy, Bass and Stern, Academic Press, 2001, 107-127]. The range of variation of E for different soft tissues can cover four orders of magnitude: from less than 1 kPa to more than 10 MPa. Even within the same tissue sample, E may change by thousands of percent during such processes as tumor development or even ordinary muscle contraction. Diseases involving fatty and/or collagenous deposits may significantly increase or decrease tissue elasticity. This substantial dependence of E on structural changes in the tissue is the basis for the palpatory diagnosis of various diseases in such human organs as prostate, thyroid, breast, liver and pelvic floor. Palpation to seek a hard lesion in soft tissue is still a widely used technique for cancer detection.

Therefore, a method that mimics manual palpation but with enhanced sensitivity and specificity might consequently lead to better diagnostics of numerous diseases. Imaging tissue elasticity using mechanical means mimicking manual palpation has been described before. For example, see an article by A. Sarvazyan, entitled "Mechanical Imaging: A new technology for medical diagnostics." Int. J. Med. Inf., 1998, 49, 195-216, which is incorporated herein in its entirety by reference. Also, elasticity imaging procedures and implementations are described in more detail in various patents of the prior art, see for example U.S. Pat. No. 5,524,636 to Sarvazyan and Skovoroda; U.S. Pat. No. 5,785,663 to Sarvazyan; U.S. Pat. No. 5,833,633 to Sarvazyan; U.S. Pat. No. 5,836,894 to Sarvazyan; U.S. Pat. No. 5,860,934 to Sarvazyan; U.S. Pat. No. 5,989,199 to Cundari et al.; U.S. Pat. No. 5,922,018 to Sarvazyan; U.S. Pat. No. 6,063,031 to Cundari et al.; U.S. Pat. No. 6,091,981 to Cundari et al.; U.S. Pat. No. 6,142,959 to Sarvazyan and Egorov; U.S. Pat. No. 6,179,790 to Cundari et al.; U.S. Pat. No. 6,468,231 to Sarvazyan and Egorov; U.S. Pat. No. 6,500,119 to West et al.; U.S. Pat. No. 6,569,108 to Sarvazyan and Egorov; U.S. Pat. No. 6,595,933 to Sarvazyan and Egorov; and U.S. Pat. No. 6,620,115 to Sarvazyan and Egorov.

A common feature of various technologies presented in these inventions is assessment of internal structure of soft tissue by measuring the surface stress patterns using a pressure sensor array pressed against the tissue. The changes in the surface stress patterns plotted as a function of displacement, applied load, and time provide information about elastic composition and geometry of the underlying tissue structures. A common name for this method and its various embodiments is "stress imaging" because this term reflects the main physical characteristic employed for visualizing tissue structures, similar to "ultrasound imaging" or "X-ray imaging".

High sensitivity of non-invasive stress imaging to pathological changes in tissue may be exploited to reduce the number of unnecessary tissue biopsies currently being performed. At the present time, several non-invasive clinical diagnostic and screening modalities such as X-ray and ultrasound imaging, magnetic resonance imaging and positron emission tomography (PET) are used for making a decision about performing a biopsy at suspicious tissue sites. In the United States alone, more than 1 million breast biopsies are performed annually and many of these biopsies appear to be unnecessary. Approximately 80% of these biopsy findings are benign. The use of stress imaging as an adjunct to other non-invasive screening and diagnostic procedures could reduce substantially this benign biopsy rate.

Various specific tissue features are used in tissue characterization depending on measured characteristics and diagnosed organ or disease. For example, ultrasonic radio frequency backscatter spectral data is used for tissue characterization as described in U.S. Pat. No. 6,238,342 to Feleppa. Ultrasonic data together with histological results of corresponding biopsy sites are stored in a database and used to train a classifier suitable for real-time tissue classification and imaging. A further method of differentiating malignant and normal tissues is based on measuring tissue impedance and comparing it with reference tissue impedance of the normal tissue as disclosed in U.S. Pat. No. 6,832,111 to Tu and Quijano. Another classifier based on a method of multivariate classification in medical diagnostics is disclosed in U.S. Pat. No. 6,868,342 issued to Mutter. Raw data is first generated by analysis of the variables and then transformed by application or appropriate algorithms to scaleless rank differentials between the variables. The rank orders of variables are used to classify tissues based on readily observable user interfaces, such as a graphical (visual) user interface or an auditory user interface.

Several other types of data classifiers are also known in the prior art, e.g. Bayesian classifiers, neural network classifiers and rule-based classifiers. A classifier is typically trained on a series of examples for a particular task. After the classifier has been so trained, new examples are presented to it for classification. The classifier can be trained either using a supervised method or an unsupervised method. For example, Parra et al. in U.S. Pat. No. 6,208,983 describe a neural network classifier for predicting a breast cancer malignancy when given patient information and skin potentials of other patients as inputs. Zhou et al. in another example teach the unified Bayesian framework for shape registration in U.S. Pat. No. 7,292,737.

One common drawback of the tissue elasticity imaging methods, including the stress imaging technique, is that they do not make full use of the wealth of diagnostic information contained in tissue mechanical features and patient-relevant data to characterize and differentiate the tissue, e.g. discriminate benign and malignant lesions. An aim of the present invention is to alleviate this drawback.

SUMMARY OF THE INVENTION

The object of the present invention is to enhance the diagnostic potential of stress imaging method and devices based on a comprehensive evaluation of mechanical properties of biological tissues, further combined with consideration of other patient-relevant data. The improved diagnostic potential of the method disclosed in this invention results from making full use of the diagnostic information contained in the plurality of structure-sensitive mechanical characteristics of examined tissue.

The novel method of tissue characterization and differentiation according to the invention includes a preliminary step of detecting the exact location of the lesion in soft tissue by analyzing in real-time an acquired sequence of stress patterns arising on the tissue surface when the probe is moved along thereof. The presence and the location of the lesion can alternatively be known in advance from X-Rays, fluoroscopy, other imaging or previous manual palpation evaluations.

The next general step is calculating at least three elasticity features characterizing the lesion such as strain hardening, loading curve average slope, lesion peak signal under a predetermined load, tissue heterogeneity, and lesion shape and mobility.

The next general step is evaluating a probability distribution for possible diagnostic outcomes for the lesion by means of a novel classifier trained using to a clinical database of cases with known diagnoses and for which all the same elasticity features were calculated as well.

The final step in the method is classification of the lesion as diseased or normal based on prevailing calculated probability for this diseased or normal condition. A subset of such classification is designating a lesion as benign or malignant.

Additionally, the classifier takes into account at least one or preferably several patient-relevant parameters such as family history of cancer disease, patient-inherited genetic factors, patient's age, weight, lifestyle and dietary factors. This allows to further improve the accuracy of differentiation between benign and malignant lesions.

DETAILED DESCRIPTION OF THE INVENTION

For the purposes of this description, the word "lesion" is used to describe a tissue portion within the main volume of tissue with mechanical properties differing from those of surrounding tissues, such as a nodule, a mass, a lump, a tumor or any other such abnormality.

A sub-set of lesions, which is of particular interest for the purposes of the invention, is a category encompassing benign and malignant lesions. Malignant (cancerous) lesion can invade and destroy nearby tissues and spread to other parts of the body. Benign (noncancerous) lesion may grow large but does not spread to other parts of the body and as a general rule does not pose a direct danger to a human life.

The present invention provides a method for enhanced characterization and differentiation of lesions into a benign or malignant. Tissue examination is generally performed by a probe having a sensor array adapted for a specific organ shape. Such probe typically incorporates an array of individual pressure sensors arranged for convenient placement in contact with the surface of the soft tissue or organ to be examined, usually with a protective cover.

Figure 1:
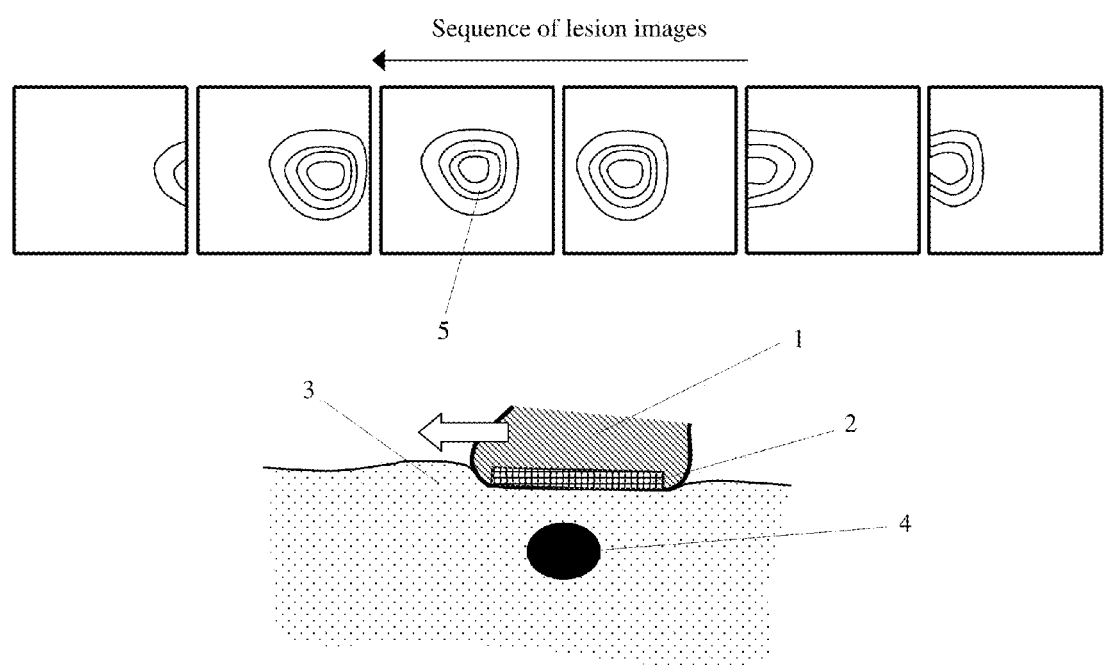
FIG. 1 shows a first optional step of the method of the invention illustrating an example of detection of tissue lesion location by a probe equipped with a pressure sensor array when the probe is moved along the tissue while applying pressure thereto.

Tissue examination is conducted over the area of clinical concern. The patient is placed in an appropriate position to access the organ of interest by the probe. A practitioner places a disposable sheath or cover over the probe, applies a lubricant to a probe sensor head or directly to the organ and starts the examination. Unless the presence and location of the lesion is known from previous examinations using an X-Ray, fluoroscopy, MRI, another imaging technique or from manual palpation examinations, the first step is to locate the lesion in the tissue. FIG. 1 schematically illustrates this step of examination. Probe 1 is equipped with a pressure sensor array 2 and moved along the surface of tissue 3 while applying some pressure thereto to detect the location of lesion 4. A sequence of lesion stress imaging data is derived in real-time from stress patterns arising on the tissue surface when it is in contact with probe 1. These images are displayed in real-time to guide the practitioner during the procedure to reveal the location of the lesion.

Figure 2:
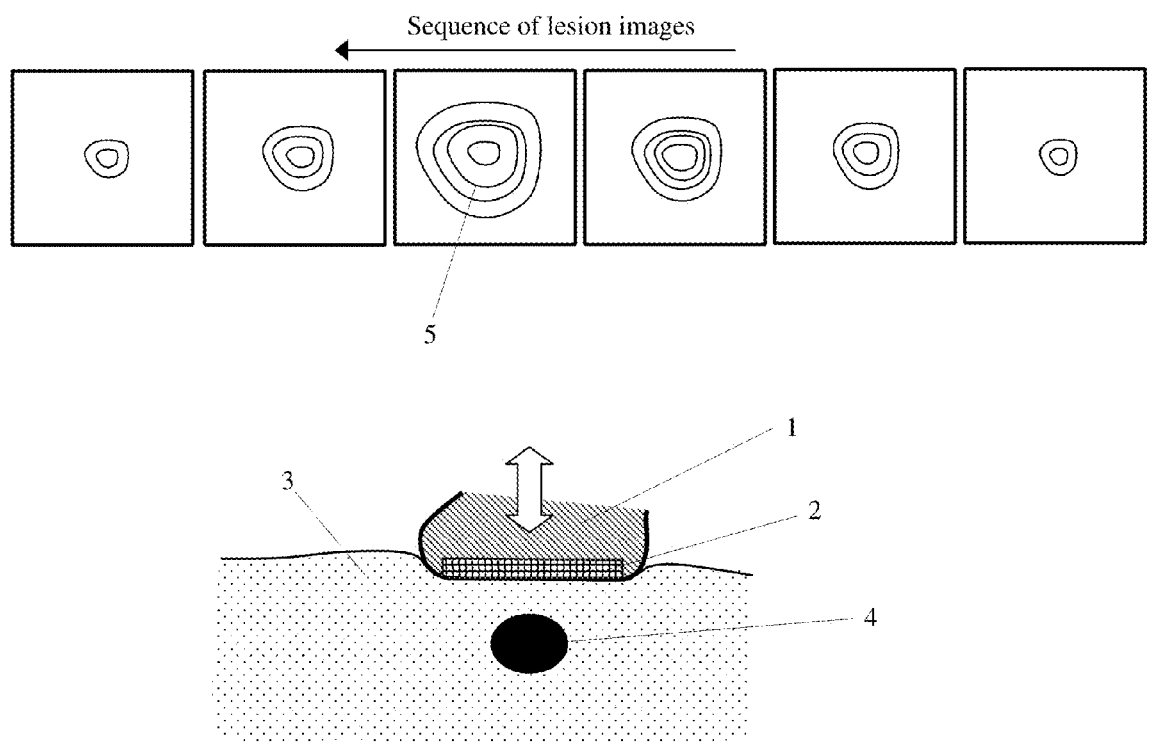
FIG. 2 shows a second step of the method with an example of probe manipulation pressing against the tissue to record a sequence of surface stress patterns effected by that lesion corresponding to an increasing compression force applied onto the probe.

In the next step, probe 1 is placed directly above the now known exact location of the lesion and a local lesion-specific scan is conducted by compressing the tissue with the probe over the location of the lesion with increasing compression force as seen on FIG. 2. During the lesion scan, a sequence of pressure-response images and surface stress patterns is acquired and processed in real-time as a function of the increasing compression force to compose an elasticity image of the lesion. The examination data is recorded and stored in a digital format file. Specific values of compression force on the probe are also recorded and correlated to each acquired surface stress pattern.

To acquire enough data, the compression of the tissue has to reach a certain minimum force so as to reveal the entire nature of the lesion. The value of that force depends on the tissue, the lesion and the depth of its location. The range of force depends on the contact area of the probe. It should be sufficient to exert pressure in the range from 2 to 20 kPa on the examined tissue, which is required to reliably produce enough stress pattern data to compute elasticity features. For example, for breast examination using the probe with the surface area of 20 cm2, the pressure range is typically from 2 kPa to 10 kPa, which corresponds to 0.4-2.0 kg of applied force.

The next step involves calculating of a number of elasticity features from these stress patterns as described in more detail below. These calculations and then supplied as inputs to a multi-parameter statistical classifier.

According to preferred embodiments of present invention, the method of non-invasive soft tissue characterization and differentiation of lesions can be used with a number of tissues and organs accessible to tactile examination both from outside the body such as a breast, thyroid and muscle tissues, and through a natural opening or passage in the body, like prostate, pelvic floor and vagina tissues, as well tissues which can be assessed during surgery, such as brain, lung, liver and kidney tissues. Tissue characterization and differentiation is often required in real-time at certain stages of surgery, such as for detecting boundary layers of diseased tissue to be treated or to be removed.

Additionally, certain aspects of the method of the invention can be applied to characterization of foreign bodies in soft tissue such as various transplants, implants, tissue-supporting mesh grids and tissue connection modules and elements.

Calculation of Elasticity Features

According to the preferred embodiment of the invention, the list of calculated elasticity features for the lesion includes at least one of the following using equations described below:

strain hardening, defined in equation (4) as the F1 factor;
loading curve average slope, defined in equation (4) as the F2 factor;
lesion peak signal under a predetermined load, defined in equation (4) as $P(Z_m)$;
tissue heterogeneity, defined in equation (5) as Hg;
lesion shape, characterized by a ration of its boundary length to the perimeter of the circle of the same area, and
lesion mobility, which is defined as M in equations (6) through (9).

The first three features are related to lesion hardness, the heterogeneity feature characterizes tissue as a whole, and two other features are parameters characterizing lesion structure and dynamics.

To calculate these features, the collected sequence of stress images or pressure patterns on the surface of the tissue during the lesion scan is plotted against a total applied force by the probe by introduction of an effective Z coordinate, which can be described as a "pressing direction", generally normal to the tissue surface. It is calculated as follows:

$$Z = \mathrm{int}\left\{A * \sum_{i=0}^{i=k} \sum_{j=0}^{j=l} S(i,j) - B\right\} \quad (1)$$

where A and B are empirical constants, k and l are numbers of pressure sensors in columns and rows of pressure sensor array respectively, and $S(i,j)$ is a pressure value measured by i,j-sensor. The empirical constants A and B are selected to provide transformation of full operational range to integer Z-scale, which defines a set of discrete layers. Each recorded stress image is ascribed to a specific Z-layer according to Equation (1). All stress images within the layer are averaged. Also, each stress image is processed independently inside the corresponding layer.

The averaged stress image in a Z-layer is denoted as Sa(x, y, Z), where x,y are orthogonal coordinates in a plane parallel to the tissue surface. In the next step, the maximum pressure value M(Z) for each Z-layer is calculated as follows:

$$M(Z) = \max\{Sa(x,y,Z)\} \quad (2)$$

Value of M(Z,) alternatively, is calculated as:

$$M(Z) = \max_{n=1 \ldots m} \{\max S(i,j,Z)\} \quad (3)$$

where $S(i,j,Z)$ is the stress image related to the Z-layer according to Equation (1); n is a number of total stress images related to the Z-layer.

Further, the values of M(Z) versus Z are considered as a loading curve and approximated by the second order polynomial P(Z):

$$P(Z) = F1*Z^2 + F2*Z + C \quad (4)$$

In the Equation (4), F1 factor characterizes nonlinearity of the loading curve and it is defined as a strain hardening of the lesion; F2 factor characterizes the average slope of the loading curve and the value of $P(Z_m)$ is the maximum pressure (lesion peak signal under a predetermined load) for the $Z_m$-layer, where the total force applied to the probe is equal to a predefined value, for example 15 N.

Tissue heterogeneity Hg is evaluated as an averaged value of Hg(t) through the examination time t:

$$Hg(t) = \sum_{i=0}^{i=l} \sum_{j=0}^{j=k} (\mathrm{abs}(S(i,j,t) - Bckg(i,j,t))/Bckg(i,j)) \quad (5)$$

where $S(i,j,t)$ is a pressure value measured by i,j-sensor at time t; $Bckg(i,j,t)$ is a background pressure pattern calculated as a second order surface for a perimeter of the stress image at time t.

Mobility of a lesion is evaluated as an averaged value of M(t) through time t for all pressure patterns containing the lesion image:

$$M(t) = \left(1 - \frac{\sum_{i=0}^{x=l} \sum_{j=0}^{y=k} Ph(i+a, j+b, Z) * Sh(i,j,t)}{\sum_{i=0}^{x=l} \sum_{j=0}^{y=l} Ph(i+a, j+b, Z)}\right) * 100\% \quad (6)$$

$$Ph(i+a, j+b, Z) = \begin{cases} 1, Sa(i+a, j+b, Z) \geq Th \\ 0, Sa(i+a, j+b, Z) < Th \end{cases} \quad (7)$$

$$Sh(i,j,t) = \begin{cases} 1, S(i,j,t) \geq Th \\ 0, S(i,j,t) < Th \end{cases} \quad (8)$$

where Th is a threshold of image binarization; $S(i,j,t)$ are elements of stress image shifted by a,b to be matched with averaged stress image produced by Sa(i+a,j+b,Z) inside Z-layer according to Equation 9. To calculate a,b values one needs to maximize functional $\Psi(a,b)$:

$$\Psi(a,b) = \sum_{i=0}^{i=k} \sum_{j=0}^{j=l} (Sa(i+a, j+b, Z) * S(i,y,t)) \quad (9)$$

The lesion mobility value (Mb), expressed in a percentage according to Equation (6), characterizes the ability of the lesion to change its form and location under mechanical indentation by the probe.

The shape of the lesion is characterized further by a ratio of lesion boundary length to the perimeter of a circle with the same area as that of the lesion visible projection.

Classifier for Differentiating Between Benign and Malignant Tissues

The present invention further discloses the use of a novel Bayesian-based statistical classifier to combine several diagnostic features and factors together. A large-scale comparison of a Bayesian classifier with the state-of-the-art algorithms for a decision tree induction and instance-based learning on standard benchmark datasets found that the simple ("naive") Bayesian classifier was superior to each of the other studied learning schemes, even on datasets with substantial feature dependencies [Rish I: An empirical study of the naive Bayes classifier. IBM Research Report RC 22230, T J Watson Research Center, Nov. 2, 2001:1-7]. The "naive" Bayesian classifier is a probabilistic classifier based on applying Bayes' theorem with strong independence (naive) assumptions. The goal of the Bayesian classification as modified by the present invention and illustrated in an example below is to calculate the probability P of a lesion being benign $C_b$ or malignant $C_m$ for a given set of lesion features F. A formal presentation of the probability looks at $P(C_i|F_j)$, where i is the lesion number and j is the lesion feature number. When the value of either $P(C_b|F_j)$ or $P(C_m|F_j)$ is greater than the other, then the classification of the lesion would be that based on the greater value. The Bayes' theorem facilitates the computation of the $P(C_i|F_j)$ probability:

$$P(C_i|F_j) = \frac{P(F_j|C_i) * P(C_i)}{P(F_j)} \quad (10)$$

where $P(C_i)$ is the prior probability of $C_i$ and $P(F_j)$ is the prior probability of $F_j$, that acts as a normalized constant often referred to as evidence. Calculation of the conditional probability $P(F_j|C_i)$ requires an estimate of joint probability distribution in n-dimensional space, where n is a number of used features on the classifier input. Under the independence assumption, the covariance matrix has only diagonal members. Hence, the conditional probability $P(F_j|C_i)$ is calculated as:

$$P(F_j|C_i) = \prod_{a=1}^{n} P(F_j^a|C_i) \quad (11)$$

where $F_j^a$ is the value of $F_j$ in the a-th dimension. For numeric data purposes, each dimension is assumed to be normally distributed, causing a need to estimate the variance $\sigma_i^a$ and mean $\mu_i^a$ for each class $C_i$ separately, directly from the clinical dataset. Once these values are computed for benign and malignant patient samples, the calculation proceeds as follows:

$$p(F_j^a|C_i) = N(F_j^a|\sigma_i^a, \mu_i^a) \quad (12)$$
$$= \exp\left(-\frac{(F_j^a - \mu_i^a)}{2(\sigma_i^a)^2}\right) / \sqrt{2\pi\sigma_i^a}$$

The value of the prior probability $P(C_i)$ is defined by the ratio of the sample size to the total number of patients. The evidence value is calculated according to:

$$P(F_j) = \sum_{a=1}^{6} (p(F_j^a|C_b) * P(C_b) + P(F_j^a|C_m) * P(C_m)) \quad (13)$$

The difference between $P(C_b|F_j)$ and $P(C_m|F_j)$ is used as a threshold parameter for the construction of the Receiver Operating Characteristic (ROC) curve.

A group of additional classifier input parameters, which can be used individually or in combination with the above listed calculated elasticity features to differentiate between benign and malignant lesions is based on patient-relevant data and includes among others the following: family history of cancer disease, patient-inherited genetic factors, history of tissue- or organ-related diseases, patient's age, weight, lifestyle and dietary factors.

Example of Implementation of the Method of the Invention

Figure 3:
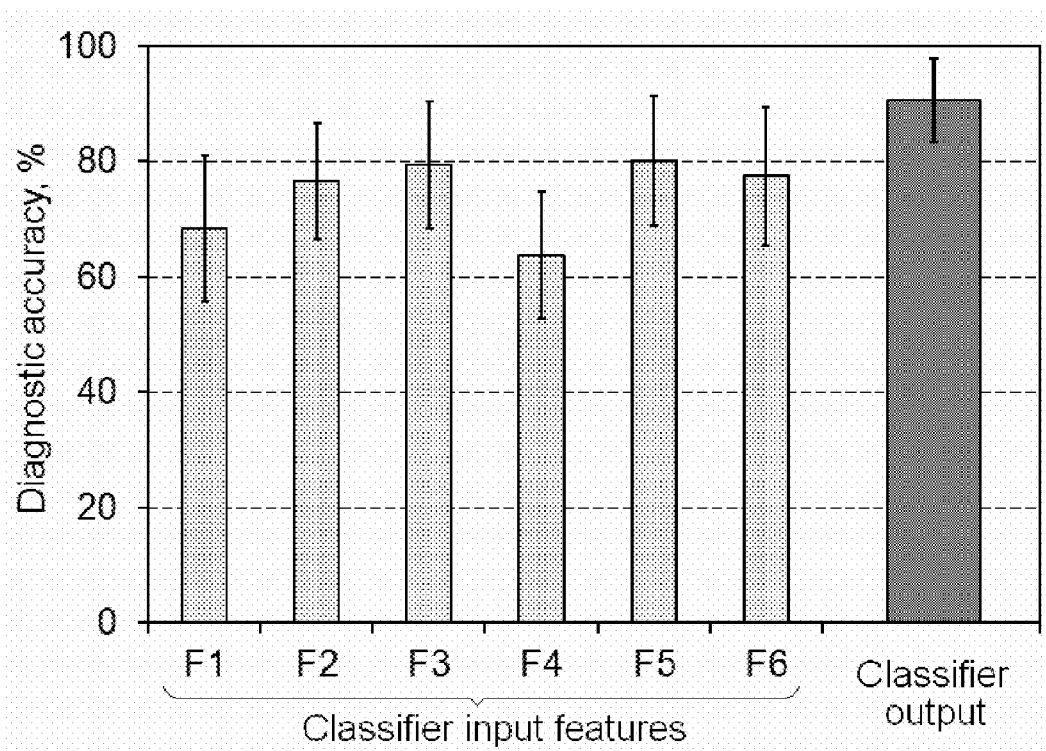
FIG. 3 shows an example of discriminating a benign breast lesion from a malignant one for a set of features and using a Bayesian classifier; and finally
Figure 4:
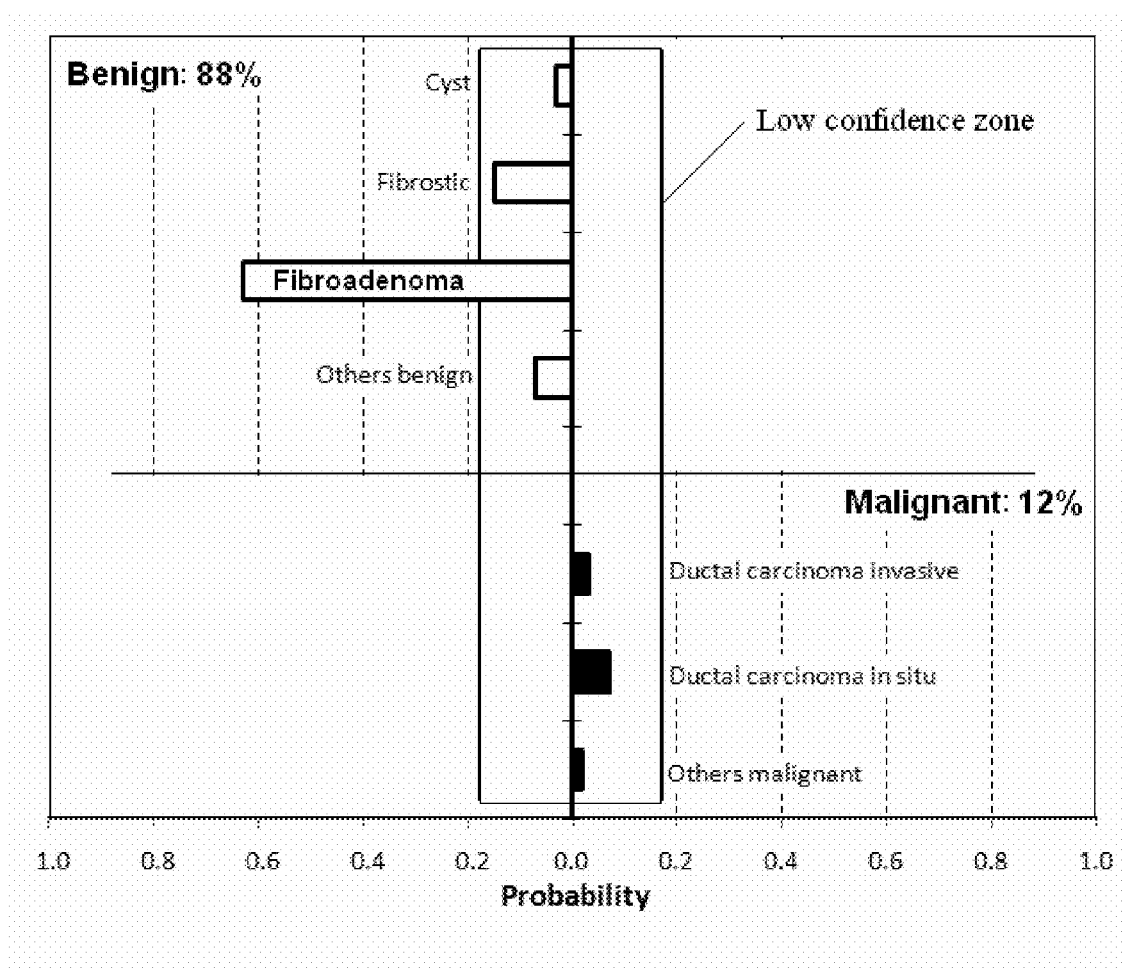
FIG. 4 shows an example of classification of a breast lesion.

FIGS. 3 and 4 illustrate an example of classification of breast lesions. The data have been collected in a clinical study with an objective to characterize and differentiate breast lesions using the method of the invention. The lesion examination data were recorded by Breast Mechanical Imager (BMI), including a probe with a pressure sensor array and an electronic unit controlled by a computer. The pressure sensor array of the probe is located as part of its head and adapted to acquire pressure patterns on the probe surface from the exterior skin layer of the breast during contact. The sensor array size is 40 mm by 30 mm comprising 192 individual pressure sensors. A clinical study of 179 patients collected data at four different clinical sites. Overall, 147 lesions were classified as benign and 32 lesions were classified as malignant based on subsequent pathology reports. They were later used in BMI data analysis as a "gold standard" reference. For all 179 cases according to Equations 1-9 above, the following lesion features were calculated:

strain hardening (F1),
loading curve average slope (F2),
lesion peak signal under a predetermined load (F3),
lesion shape (F4), and
lesion mobility (F5).

Patient age (F6) has been included in the list of parameters used for characterization and differentiation. The area under the ROC curve (AUC), characterizing the discrimination of benign and malignant lesions, was calculated separately for each feature of the set F1-F6 as displayed in FIG. 3. This plot demonstrates the diagnostic effectiveness of the analyzed features.

The set of features F1-F6 was then used as an input to the Bayesian classifier described by Equations 10-13. The classifier output is shown on FIG. 3. As illustrated on that figure, the diagnostic accuracy is increased from 63-80% for individual features to 91% for classier output and confidence interval (vertical error bars) is decreased from 21-27% for individual features to less than 15% for classier output.

FIG. 4 demonstrates the probability distribution for extended set of possible clinical outcomes for one particular lesion obtained using a Bayesian classifier adjusted for multiple diagnoses on the basis of clinical data for 179 known outcomes. This multi-patient classification has a low confidence zone, which removes diagnostic consideration of outcomes with low probability. The binary differentiation for this case is done by summation of all benign and malignant probabilities yields to the following ratio: 88% for benign and 12% for malignant.

While the invention has been described with reference to a specific embodiment, the description is illustrative of the invention and is not to be construed as limiting the scope of the claims. Various modifications and applications may occur to those who are skilled in the art, without departing from the true spirit and scope of the present invention, which is defined only by the appended claims.

What is claimed is:

1. A method of soft tissue characterization and soft tissue differentiation comprising the steps of:
    (a) detecting a lesion in said tissue;
    (b) applying an increasing compression force over said lesion and collecting a sequence of stress patterns as a function of said increasing compression force;
    (c) calculating from said sequence of stress patterns at least three elasticity features characterizing said lesion, said elasticity features selected from a group consisting of strain hardening, loading curve average slope, lesion peak signal under a predetermined load, tissue heterogeneity, lesion shape and lesion mobility;
    (d) inputting said at least three calculated elasticity features into a statistical classifier to calculate probabilities of possible diagnostic outcomes, said statistical classifier created in advance using a dataset of previously collected samples with known clinical status, said samples having been collected from several patients and including data on elasticity features that are the same as said at least three calculated elasticity features; and (e) selecting a diagnostic outcome with prevailing calculated probability for providing a diagnosis of said soft tissue.

2. The method as in claim 1, wherein step (b) further includes providing a pressure probe equipped with a pressure sensor array adapted to be placed against and compress said tissue, step (b) further including acquiring stress patterns from the surface of said tissue in real-time.

3. The method as in claim 2, wherein said step (a) further includes acquiring stress imaging data in real-time by moving said pressure probe along said tissue.

4. The method as in claim 1, wherein said tissue is selected from a group consisting of thyroid tissue, breast tissue, prostate tissue, pelvic floor tissue, brain tissue, lung tissue, liver tissue, kidney tissue, and muscle tissue.

5. The method as in claim 1, wherein said lesion peak signal under a predetermined load is calculated in step (c) while values of a maximum pressure versus said compression force against said tissue are considered as a loading curve and approximated by a second order polynomial to characterize strain hardening of said tissue.

6. The method as in claim 1, wherein said step (d) further includes said statistical classifier calculating a probability for said lesion to be either benign or malignant.

7. The method as in claim 1, wherein said step (d) further includes at least one patient-related parameter as an additional input to said statistical classifier.

8. The method as in claim 1, wherein said steps (a) through (e) are performed during surgery, said surgery providing direct access to said tissue.

9. The method as in claim 1, wherein said statistical classifier is a Bayesian classifier.

10. The method as in claim 9, wherein said statistical classifier is a naive Bayesian classifier.

11. A method of soft tissue characterization and soft tissue differentiation comprising the steps of:
(a) detecting a lesion and a lesion location in said tissue;
(b) applying an increasing compression force over said lesion location and collecting a sequence of stress patterns, said sequence of stress patterns being a function of said increasing compression force;
(c) calculating from said sequence at least three elasticity features characterizing said lesion;
(d) generating a probability distribution for possible diagnostic outcomes for said lesion by inputting said at least three elasticity features into a statistical classifier created using a clinical database of cases from several patients (i) having known diagnoses and (ii) including data on elasticity features that are the same as said at least three calculated elasticity features; and
(e) providing a diagnosis of said soft tissue based on the diagnostic outcome with prevailing calculated probability.

12. The method as in claim 11, wherein step (b) further includes providing a pressure probe equipped with a pressure sensor array adapted to be placed against and compress said tissue, step (b) further including acquiring stress patterns from the surface of said tissue in real-time.

13. The method as in claim 12, wherein said step (a) further includes acquiring stress imaging data in real-time by moving said pressure probe along said tissue.

14. The method as in claim 11, wherein said tissue is selected from a group consisting of thyroid tissue, breast tissue, prostate tissue, pelvic floor tissue, brain tissue, lung tissue, liver tissue, kidney tissue, and muscle tissue.

15. The method as in claim 11, wherein said lesion peak signal under a predetermined load is calculated in step (c) while values of a maximum pressure versus said compression force against said tissue are considered as a loading curve and approximated by a second order polynomial.

16. The method as in claim 11, wherein said step (d) further includes said statistical classifier calculating a probability for said lesion to be either benign or malignant.

17. The method as in claim 11, wherein said step (d) further includes inputting at least one patient-related parameter into said statistical classifier in order to evaluate said probability distribution for possible diagnostic outcomes for said lesion, said statistical classifier being further created using a clinical database of cases (iii) including data on a parameter that is the same as the at least one patient-related parameter.

18. The method as in claim 11, wherein said steps (a) through (e) are performed during surgery, said surgery providing direct access to said tissue.

19. The method as in claim 11, wherein said statistical classifier is a Bayesian classifier.

20. The method as in claim 19, wherein said statistical classifier is a naive Bayesian classifier.

21. The method as in claim 11, wherein said at least three elasticity features are selected from a group consisting of strain hardening, loading curve average slope, lesion peak signal under a predetermined load, tissue heterogeneity, lesion shape and lesion mobility.

22. The method of claim 17, wherein said at least one patient-related parameter is selected from a group consisting of a family history of cancer disease, a patient-inherited genetic factor, a history of said tissue related diseases, patient's age, patient's weight, and patient's lifestyle and dietary factors.

23. The method of claim 7, wherein said at least one patient-related parameter is selected from a group consisting of a family history of cancer disease, a patient-inherited genetic factor, a history of said tissue related diseases, patient's age, patient's weight, and patient's lifestyle and dietary factors.

24. A method of soft tissue characterization and soft tissue differentiation comprising the steps of:
(a) detecting a lesion in said tissue;
(b) compressing said tissue over said lesion with an increasing compression force and collecting a sequence of stress patterns as a function of said increasing compression force;
(c) calculating from said sequence of stress patterns at least three elasticity features characterizing said lesion;
(d) generating a probability distribution for possible diagnostic outcomes for said lesion by inputting said at least three elasticity features into a statistical classifier created using a clinical database of cases from several patients (i) having known diagnoses and (ii) including data on elasticity features that are the same as said at least three calculated elasticity features; and
(e) providing a diagnosis of said soft tissue based on said probability distribution.

* * * * *